US010525797B2

(12) United States Patent
Maeda et al.

(10) Patent No.: US 10,525,797 B2
(45) Date of Patent: Jan. 7, 2020

(54) VEHICLE ANTIFOGGING SYSTEM

(71) Applicant: MAZDA MOTOR CORPORATION, Hiroshima (JP)

(72) Inventors: Tetsuya Maeda, Hiroshima (JP); Daiji Katsura, Hiroshima (JP)

(73) Assignee: MAZDA MOTOR CORPORATION, Hiroshima (JP)

( * ) Notice: Subject to any disclaimer, the term of this patent is extended or adjusted under 35 U.S.C. 154(b) by 0 days.

(21) Appl. No.: 16/042,614

(22) Filed: Jul. 23, 2018

(65) Prior Publication Data
US 2019/0030997 A1 Jan. 31, 2019

(30) Foreign Application Priority Data
Jul. 28, 2017 (JP) .................... 2017-146856

(51) Int. Cl.
| | | |
|---|---|---|
| *B60J 1/00* | (2006.01) | |
| *G01N 27/12* | (2006.01) | |
| *B60S 1/02* | (2006.01) | |
| *C03C 17/28* | (2006.01) | |
| *C09K 3/18* | (2006.01) | |

(52) U.S. Cl.
CPC .......... *B60J 1/002* (2013.01); *G01N 27/121* (2013.01); *B60S 1/026* (2013.01); *C03C 17/28* (2013.01); *C08G 2290/00* (2013.01); *C09K 3/185* (2013.01)

(58) Field of Classification Search
CPC ... B60J 1/002; G01N 27/121; B60H 1/00785; B60H 3/024; B60S 1/026; C03C 17/28; C03C 17/32; C08G 2290/00; C09K 3/185
USPC ........................................................ 52/171.2
See application file for complete search history.

(56) References Cited

U.S. PATENT DOCUMENTS

| | | | | | |
|---|---|---|---|---|---|
| 1,936,776 | A | * | 11/1933 | Swain | B60S 1/54 237/12.3 R |
| 3,968,342 | A | * | 7/1976 | Inaba | G01N 27/121 219/203 |
| 3,995,140 | A | * | 11/1976 | Kuiff | H05B 3/84 219/203 |
| 4,150,443 | A | * | 4/1979 | McNeilly | A61F 9/028 2/171.3 |
| 4,321,296 | A | * | 3/1982 | Rougier | B32B 17/10018 219/203 |

(Continued)

FOREIGN PATENT DOCUMENTS

| | | | |
|---|---|---|---|
| DE | 19942286 C1 * | 8/2000 | ......... B60H 1/00785 |
| DE | 102016119141 A1 * | 4/2017 | ......... B60H 1/00785 |
| JP | 4670418 B2 | 4/2011 | |

*Primary Examiner* — Patrick J Maestri
*Assistant Examiner* — Joseph J. Sadlon
(74) *Attorney, Agent, or Firm* — Studebaker & Brackett PC

(57) ABSTRACT

An antifogging system of a vehicle includes a windshield provided between a space inside a vehicle cabin and a space outside the vehicle cabin, an antifogging coating provided on a surface of the windshield facing the vehicle cabin and configured to absorb water adhering to a surface the coating into the coating, an air conditioner configured to vaporize water absorbed in the antifogging coating, a humidity sensor configured to detect a humidity in a temperature boundary layer formed along a surface of the antifogging coating facing the vehicle cabin, and a control unit configured to operate the air conditioner when the humidity is equal to or higher than a predetermined threshold.

6 Claims, 9 Drawing Sheets

(56) References Cited

U.S. PATENT DOCUMENTS

| | | | | |
|---|---|---|---|---|
| 4,576,864 | A * | 3/1986 | Krautter | C09K 3/18 428/328 |
| 4,604,946 | A * | 8/1986 | Watanabe | B60H 1/242 454/127 |
| 4,917,293 | A * | 4/1990 | Fedter | B60H 1/00764 165/202 |
| 4,920,755 | A * | 5/1990 | Tadahiro | B60H 1/00785 165/223 |
| 5,056,817 | A * | 10/1991 | Fuller | B60R 99/00 150/166 |
| 6,138,749 | A * | 10/2000 | Kawai | B60H 1/00064 165/204 |
| 6,313,454 | B1 * | 11/2001 | Bos | B60H 1/00785 165/233 |
| 7,900,464 | B2 * | 3/2011 | Aoki | B60H 1/00785 165/233 |
| 9,862,317 | B2 * | 1/2018 | Fragoso Iniguez | B32B 17/10018 428/213 |
| 10,272,745 | B2 * | 4/2019 | Kataoka | B60H 1/00785 |
| 2007/0235549 | A1 * | 10/2007 | Nakajima | B60H 1/00785 236/44 R |
| 2010/0068486 | A1 * | 3/2010 | Kayanoki | B32B 17/10018 428/213 |
| 2013/0183894 | A1 * | 7/2013 | Watanabe | B01D 53/261 454/127 |
| 2017/0106721 | A1 * | 4/2017 | Hoke | B60H 1/00785 |

\* cited by examiner

VEHICLE ANTIFOGGING SYSTEM

CROSS-REFERENCE TO RELATED APPLICATION

This application claims priority to Japanese Patent Application No. 2017-146856 filed on Jul. 28, 2017, the entire disclosure of which is incorporated by reference herein.

BACKGROUND

The present disclosure relates to a vehicle antifogging system.

Generally, dew condensation occurs on a surface of a window mounted to a vehicle when it rains or snows or in other situations. Such dew condensation, i.e., formation of water droplets on the window surface by moisture in the atmosphere, is caused when the temperature of one of the surfaces of the window becomes lower than the dew point due to the atmospheric temperature and humidity inside and outside the window, or when the window is subjected to a sudden change in temperature. The dew condensation causes scattering of light transmitted through the window, and consequently causes fog. Fog occurring on the window obstructs the driver's field of view, and may impede the driving.

When fog occurs on the window due to dew condensation, a defroster vaporizes the water adhering to the internal surface of the window to defog the window. For example, the defroster is configured to defog the window by sending, from an air outlet of the defroster, conditioning airflow to the internal surface of the window while sucking outdoor air having a low humidity, as a compressor of an air conditioning unit is driven by a power source and an evaporator functions as a dehumidifier.

As can be seen, since ventilation takes place when the defroster operates to defog the window, the temperature in the vehicle cabin decreases, in particular, in cold weather. In such a situation, a thermal load is required to return the vehicle cabin temperature after the ventilation to an appropriate temperature.

Meanwhile, in recent years, it has been required to reduce the thermal load for maintaining the temperature in the vehicle cabin at an appropriate temperature, in view of the need of, for example, regulation of carbon dioxide emission and improvement of fuel economy. As discussed above, the load of ventilation (specifically, the ventilation taking place when outdoor air is sucked to operate the defroster) to defog the window constitutes a large percentage of the thermal load in cold weather. Reducing the operation of the defroster causing the ventilation load enables effective reduction in thermal load, and is expected to improve the fuel economy.

For this reason, to reduce the operation frequency and/or the operation time of the defroster, a technique for making a vehicle window resistant to fogging is proposed: it is proposed to provide a window with antifogging treatment, i.e. formation of a special coating on the window. Specifically, an exemplary window provided with such antifogging treatment has, on its surface, a hydrophilic, water-slipping or water-absorptive coating, and is resistant to dew condensation that causes fog. Thus, use of this antifogging means causing no thermal load leads to reduction of the ventilation load.

In the case of using a hydrophilic coating, water adhering to a surface of the coating forms a film, reducing the formation of water droplets. In the case of using a water-slipping coating, water droplets on a surface of the coating slip down along the coating. In the case of using a water-absorptive coating, water adhering to the surface of the coating is absorbed into the coating, reducing the formation of water droplets.

Using these antifogging coatings reduces scattering of light caused by water droplets on the window, and accordingly, can reduce the operation opportunities and/or the operation time of the defroster.

Among the antifogging coatings described above, the water-absorptive coating has received attention because it advantageously makes it difficult for water droplets to remain on the surface, and for the absorbed water to freeze in the coating.

In the case of using the water-absorptive coating, when the quantity of water absorbed in the coating reaches the largest possible quantity that can be absorbed in the coating (hereinafter referred to as the "saturated water absorption volume"), the coating no longer can absorb water, and water droplets form on the surface of the coating.

With respect to this problem, for example, Japanese Patent No. 4670418 discloses a technique of detecting a quantity of water contained in a coating, and operating a defroster when the quantity of water reaches a predetermined quantity, so as to vaporize the water in the coating. This technique enables recovery of the water absorptive capacity of the coating by operating the defroster according to the quantity of water in the coating.

SUMMARY

However, in the antifogging device disclosed in the publication described above, the quantity of water absorbed in the antifogging coating is used as a parameter, and the defroster operates whenever the quantity of water is equal to or larger than the predetermined value. For this reason, the defroster operates even in a situation where the operation of the defroster is unnecessary: for example, in an environment in which the humidity in the vehicle cabin is low and water droplets are quickly dried without operating the defroster, or in an environment in which the surface temperature of the coating is high, such as in summer, and the saturated water absorption volume of the coating increases. Even in these situations, the defroster operates when the quantity of water reaches or exceeds the threshold, which may cause an energy loss.

On the other hand, the defroster is needed to operate to prevent fogging, for example, when the humidity in the vehicle cabin increases suddenly. Even in such a situation, if the quantity of water is smaller than the threshold, the defroster does not operate, and the antifogging capability of the antifogging coating cannot prevent fogging.

The present disclosure relates to an antifogging system for a vehicle including an antifogging coating, the antifogging system reducing unnecessary operation while operating efficiently as needed, thereby enabling improvement of fuel economy of the vehicle and visibility for a passenger.

Specifically, a vehicle antifogging system disclosed herein includes:

a window provided between a space inside a vehicle cabin and a space outside the vehicle cabin;

an antifogging coating provided on a surface of the window facing the vehicle cabin, and configured to absorb water adhering to a surface the antifogging coating into the antifogging coating;

a dryer configured to vaporize the water absorbed in the antifogging coating; a humidity detector configured to detect a humidity in a temperature boundary layer formed along a surface of the antifogging coating facing the vehicle cabin; and a controller configured to operate the dryer when the humidity is equal to or higher than a predetermined threshold.

The "temperature boundary layer" as used herein is a layer formed between the antifogging coating and a portion, of the vehicle cabin space, in which the temperature is stable. In the temperature boundary layer, the temperature approaches the temperature of the vehicle cabin space with increase in the distance from the antifogging coating.

The "threshold" as used herein is a value determined based on a response speed of the humidity detector and an operation speed of the dryer. For example, the threshold of humidity is set to be a value of 90% or more.

In this configuration, the vehicle window is provided with the antifogging coating, and the dryer operates when the humidity in the temperature boundary layer formed along the surface of the antifogging coating facing the vehicle cabin reaches the predetermined threshold. In the temperature boundary layer, the temperature and the humidity are different from those in a space inside the vehicle cabin and located outside the region of the temperature boundary layer, and likelihood of increase in the humidity varies depending on the quantity of water absorbed in the antifogging coating. For this reason, the humidity in the temperature boundary layer is adopted as a parameter indicating the likelihood of occurrence of fog on the surface of the antifogging coating, and the operation of the dryer is controlled based on the humidity in the temperature boundary layer. This configuration enables effective reduction of occurrence of fog on the surface of the antifogging coating, while enabling reduction in the operation frequency and the operation time of the dryer. Thus, this configuration enables both reduction of an energy loss and improvement in visibility.

The humidity detector may detect a humidity in a part of the space inside the vehicle cabin, and the part extends 3 mm or less from the surface of the antifogging coating facing the vehicle cabin.

The humidity detector may be positioned at a distance of 0.05 mm or more from the surface of the antifogging coating facing the vehicle cabin.

Positioning the humidity detector at a distance of 0.05 mm or more from the surface of the antifogging coating facing the vehicle cabin substantially prevent the humidity detector from disturbing airflow on the surface of the antifogging coating.

The vehicle antifogging system may further include:

a water quantity detector configured to detect a quantity of water absorbed in the antifogging coating; and a corrector configured to correct the humidity based on the water quantity, wherein the controller may operate the dryer when the humidity corrected by the corrector is equal to or higher than the threshold.

After the humidity detected by the humidity detector is corrected based on the water quantity detected by the water quantity detector, and the corrected humidity is used as a parameter to operate the dryer. This configuration enables control of the dryer, with the water quantity absorbed in the antifogging coating taken into account. This makes it possible to more effectively reduce the operation frequency and operation time of the dryer, contributing to more effective reduction of the energy loss.

The dryer may blow dry air over the surface of the antifogging coating.

With configuring in which the dryer blows dry air over the surface of the antifogging coating, a conventional air conditioner can be used to prevent deterioration of visibility for the driver.

The dryer may be provided on the window, and generate heat by causing a current to flow through a conductor, and the conductor may be provided inside the window, at an interface between the window and the antifogging coating, or on the surface of the antifogging coating facing the vehicle cabin.

With the configuration in which the dryer causes the conductor to generate heat, if the conductor is provided inside the window or at the interface between the window and the antifogging coating, a conventional electric heater can be used to prevent deterioration of visibility for the driver. If the conductor is provided at the interface between the window and the antifogging coating or on the surface of the antifogging coating facing the vehicle cabin, the antifogging coating can be directly heated, thereby effectively remove the water absorbed in the antifogging coating.

The window may be made of light-transmitting glass or resin.

DETAILED DESCRIPTION

Embodiments of the present disclosure will be described below.

Figure 1:
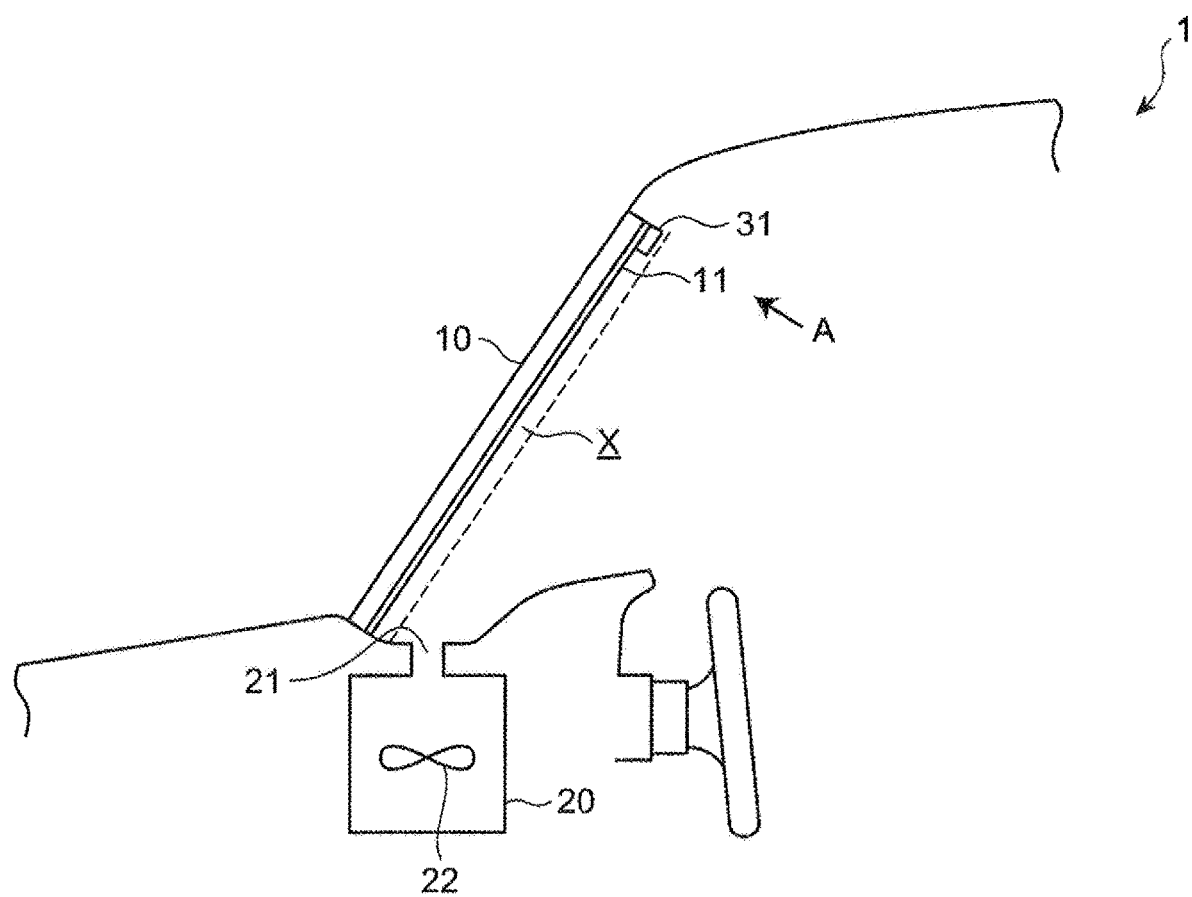
FIG. 1 is a schematic side view of a vehicle including an antifogging coating according to a first embodiment.
Figure 2:
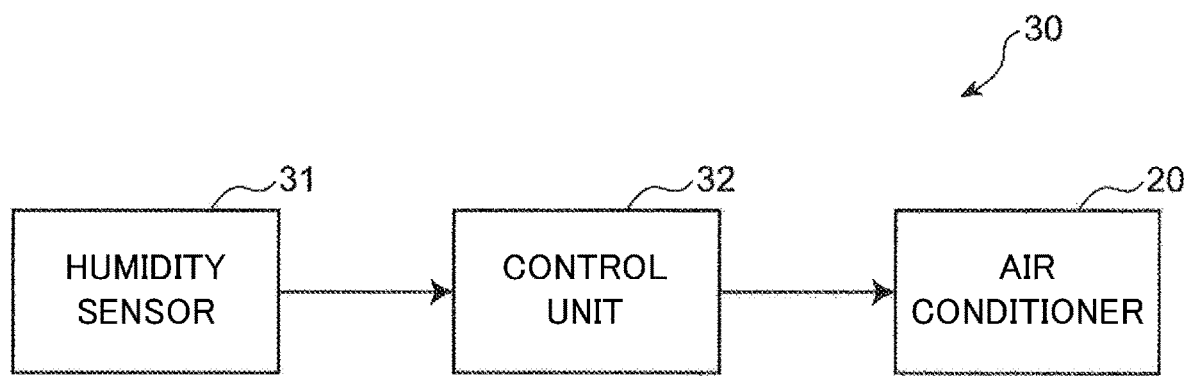
FIG. 2 is a system diagram of a vehicle antifogging system including the antifogging coating according to the first embodiment.

As illustrated in FIGS. 1 and 2, a vehicle 1 according to an embodiment includes a windshield 10, an air conditioner 20 configured to condition air in a vehicle cabin, and an antifogging system 30 configured to defog the windshield 10. The windshield 10 is made of a plate-shaped member for a window, such as glass or resin.

The air conditioner 20 includes a defroster air outlet 21 from which conditioning airflow is blown along a surface of the windshield 10 facing the vehicle cabin, and a blower fan 22 configured to supply the conditioning airflow from the defroster air outlet 21. The air conditioner 20 functions as a dryer that dries the windshield 10.

The antifogging system 30 includes the air conditioner 20 functioning as the dryer, and an antifogging coating 11 provided on the surface of the windshield 10 facing the vehicle cabin. The antifogging coating 11 is a water-absorptive layer formed on the surface of the windshield 10 facing the vehicle cabin. The antifogging coating 11 is made of a resin material having water absorptivity.

The antifogging system 30 further includes a humidity sensor 31 arranged on a side, of antifogging coating 11 on the windshield 10, facing the vehicle cabin, and a control unit 32 configured to control the air conditioner 20. The humidity sensor 31 is disposed in a region of a temperature boundary layer X formed along the surface of the antifogging coating 11 facing the vehicle cabin. The humidity sensor 31 detects a humidity and outputs to the detected humidity to control unit 32.

The temperature boundary layer X is a layer between the antifogging coating 11 and a portion, of the vehicle cabin space, in which the temperature is stable. The temperature in the temperature boundary layer X approaches the temperature of the vehicle cabin space with increase in the distance from the antifogging coating 11.

The control unit 32 is configured to operate the air conditioner 20 when the humidity detected by the humidity sensor 31 exceeds a predetermined threshold.

The threshold is a value determined based on a response speed of the humidity sensor 31 and an operation speed of the air conditioner 20. For example, the threshold of humidity is set to be a value of 90% or more.

Here, the temperature boundary layer X will be described in detail with reference to FIGS. 3 and 4.

Figure 3:
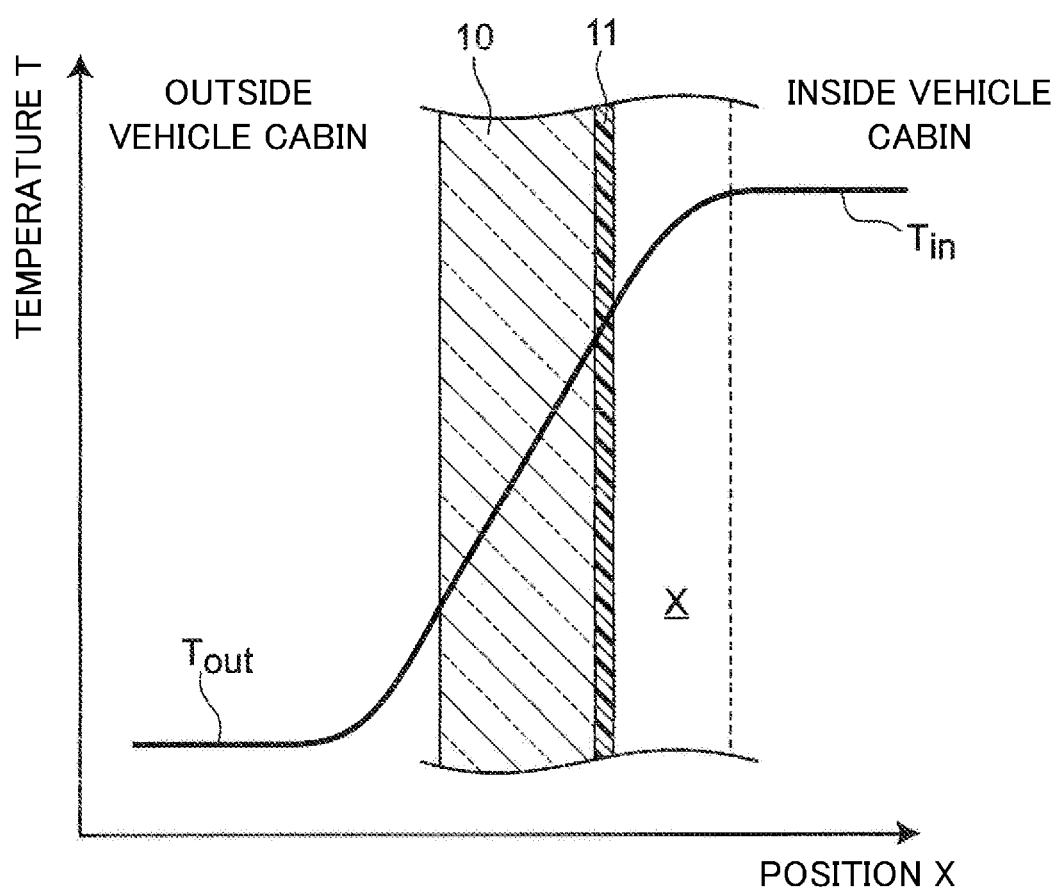
FIG. 3 illustrates a change in temperature from outside to inside of a vehicle cabin.

In FIG. 3, the reference character "Tout" denotes a temperature outside the vehicle cabin (outside temperature), and the reference character "Tin" denotes a temperature inside the vehicle cabin.

FIG. 3 illustrates a general trend of temperature distribution in a region from the outside to the inside of the vehicle cabin, with the windshield 10 separating the inside from the outside, in an environment in which the temperature Tout outside the vehicle cabin is lower than the temperature Tin inside the vehicle cabin. As illustrated in FIG. 3, the windshield 10 and a space adjacent thereto have a temperature distribution in which the temperature increases toward the inside of the vehicle cabin. In the vehicle cabin, a space near the antifogging coating 11 has a temperature distribution in which the temperature rises with increase in the distance from the surface of the coating 11, and a space more distant from the windshield than the space near the antifogging coating 11 is has a uniform temperature distribution in which the temperature is substantially constant.

As can be seen, the temperature boundary layer X has a temperature environment different from that of a portion, of the vehicle cabin space, located outside the region of the temperature boundary layer X. In winter, the temperature boundary layer X, which has a lower temperature and a lower saturated vapor volume than the vehicle cabin space outside the region of the temperature boundary layer X, tends to have a high humidity.

In addition, the present inventors have made the following findings: in the case where the water-absorptive antifogging coating 11 is formed on the windshield 10, likelihood of increase in the humidity in the temperature boundary layer X varies depending on the quantity of water absorbed in the antifogging coating 11. Specifically, when the quantity of water absorbed in the antifogging coating 11 is relatively small, since the antifogging coating 11 tends to absorb the water vapor in the temperature boundary layer X, the humidity in the temperature boundary layer X is less likely to increase. By contrast, when the quantity of water absorbed in the antifogging coating 11 reaches the saturated water absorption volume, since the antifogging coating 11 can no longer absorb water, the humidity in the temperature boundary layer X is more likely to increases.

Thus, the humidity in the temperature boundary layer X is a parameter influenced by the temperature in the temperature boundary layer X and the quantity of water absorbed in the antifogging coating 11. Focusing on this, the present inventors have conceived of defogging the surface of the antifogging coating 11 by controlling the operation of the air conditioner 20 based on the humidity in the temperature boundary layer X.

In addition, it has been found that the thickness of the temperature boundary layer X from the surface of the antifogging coating 11 on the windshield 10 varies according to change in convective heat transfer coefficient inside the vehicle cabin.

Figure 4:
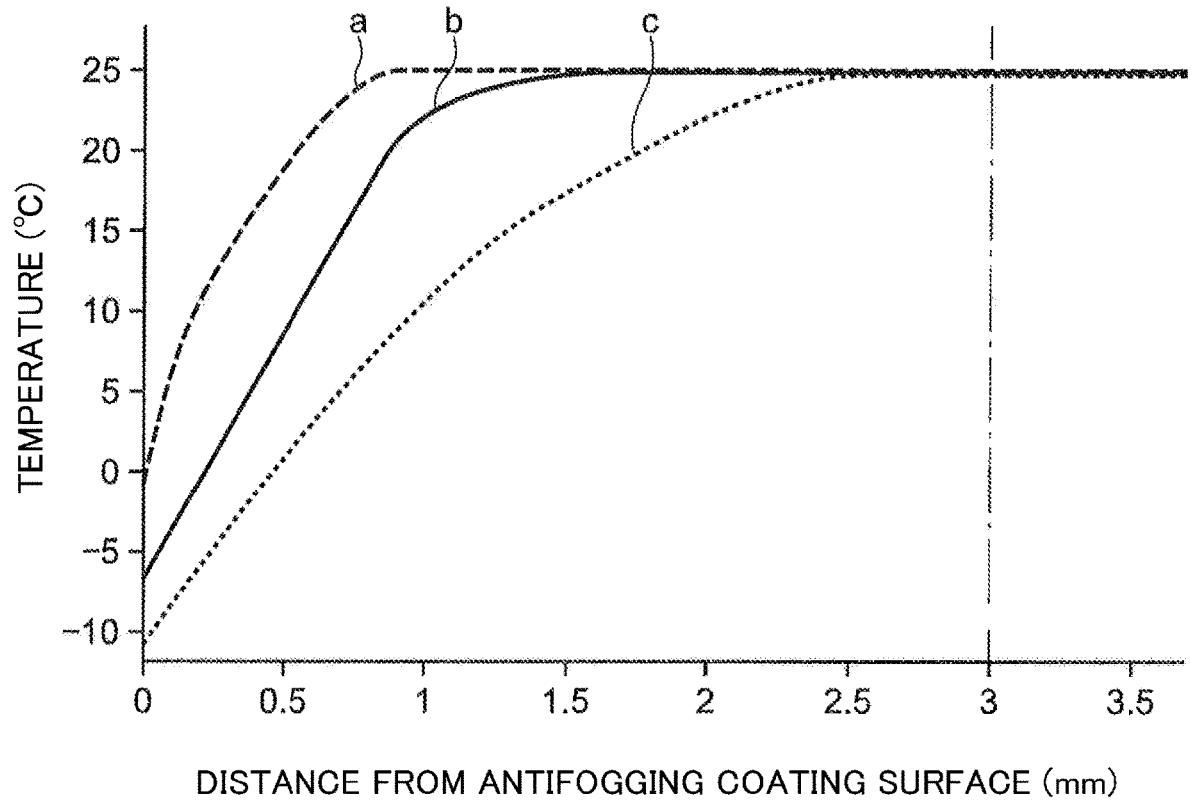
FIG. 4 illustrates experimental and theoretical values for detection of changes in a temperature boundary layer according to different levels of intensity of heating.

For this reason, as illustrated in FIG. 4, on the assumption that the air conditioner 20 performs heating in winter, the present inventors have obtained, experimentally and theoretically, data about variation in thickness of the temperature boundary layer X according to change in convective heat transfer coefficient, by setting the heating intensity of the air conditioner 20 to three levels, namely "strong a," "medium b," and "weak c."

FIG. 4 shows variation in temperature according to positions in a region from the surface of the antifogging coating 11 on the windshield 10 to the vehicle cabin space in the cases where the heating intensity of the air conditioner 20 is set to "strong a", "medium b", and "weak c." For the heating intensity of "medium b," the values measured in the experiment were used. With respect to the heating intensities of "strong a" and "weak c" of the air conditioner 20, the thickness L of the temperature boundary layer X was calculated on the basis of a thermal conductivity of air $\lambda$air, the temperature Tin inside the vehicle cabin detected by a vehicle cabin temperature sensor, the temperature Twin of the surface of the antifogging coating 11 facing the vehicle cabin, an amount of heat Q passing through the windshield 10 from the outside to the inside of the vehicle cabin, and according to the following Expression 1.

$$L = \lambda \text{air} \times (T\text{in} - T\text{win})/Q \quad (1)$$

The temperature Twin of the surface of the antifogging coating 11 facing the vehicle cabin in Expression 1 is determined based on the temperature Tin inside the vehicle cabin, the temperature Tout outside the vehicle cabin, the vehicle speed detected by a vehicle speed sensor, the output of the blower fan 22 acquired by an air conditioner controller controlling the air conditioner 20, the convective heat transfer coefficient $\alpha$in between the surface of the windshield 10 facing the vehicle cabin and the air in the vehicle cabin, the amount of heat Q passing through the windshield 10 from the outside to the inside of the vehicle cabin, and according to the following Expression 2.

$$T\text{win} = T\text{in} - Q/\alpha\text{in} \quad (2)$$

The amount of heat Q passing from the outside to the inside of the vehicle cabin is determined based on the convective heat transfer coefficient $\alpha$out between the surface of the windshield 10 facing outside and air outside the vehicle cabin, the thermal conductivity $\lambda$ of the windshield 10, the thickness 1 of the windshield 10, the convective heat transfer coefficient $\alpha$in, the temperature Tout outside the vehicle cabin, and the temperature Tin inside the vehicle cabin, and according to following Expression 3.

$$Q = (T\text{in} - T\text{out})/(1/\alpha\text{in} + 1/\lambda + 1/\alpha\text{out}) \quad (3)$$

The convective heat transfer coefficient αout and a wind velocity outside the windshield 10 determined from the vehicle speed have a relationship that the convective heat transfer coefficient αout increases as the wind velocity increases. The convective heat transfer coefficient αin and an airflow speed inside the windshield glass 10 determined from the output of the blower fan 22 have a relationship that the convective heat transfer coefficient αin increases as the airflow speed increases. Specifically, in this calculation, the convective heat transfer coefficient inside the vehicle for the strong level of the heating intensity is given as αin=20 W/m²K, and the convective heat transfer coefficient inside the vehicle cabin for the weak level of the heating intensity is given as αin=5 W/m²K.

According to the result, when the heating intensity is set to the strongest level, as indicated by the broken line a in FIG. 4, temperature distribution in the vehicle cabin is such that the temperature is the lowest at the surface of the windshield facing the vehicle cabin, and increases toward the inside of the vehicle cabin, and then, is substantially constant from a position distant by 0.97 mm from the surface of the windshield facing the vehicle cabin. When the heating intensity is set to the medium level, as indicated by the solid line b in FIG. 4, the temperature distribution in the vehicle cabin is such that the temperature is substantially constant from a position distant by 1.7 mm from the surface of the windshield facing the vehicle cabin. When the heating intensity is set to a level weaker than the medium level, as indicated by the dot line c in FIG. 4, temperature distribution in the vehicle cabin is such that the temperature is substantially constant from a position distant by 2.52 mm from the surface of the windshield facing the vehicle cabin.

Accordingly, in the situation of any of the experiments, the temperature boundary layer X is presumed to cover a region from the surface of the antifogging coating 11 to a position distant from the surface by a predetermined distance smaller than 3.0 mm.

Figure 5A:
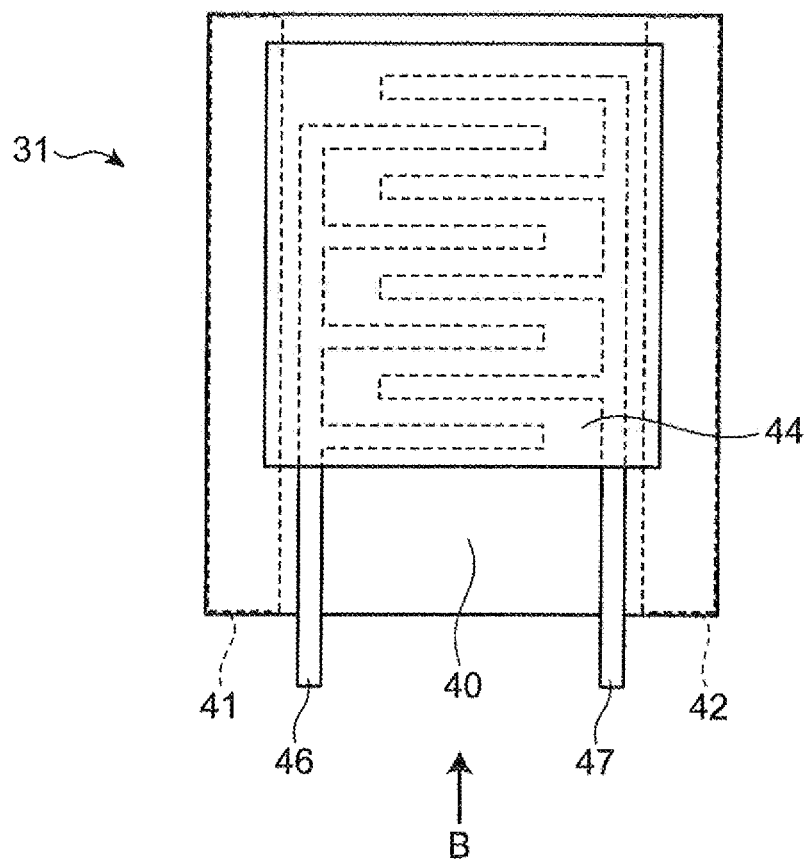
FIGS. 5A and 5B are diagrams illustrating an exemplary structure of a polymer-based resistive humidity sensor.
Figure 5B:
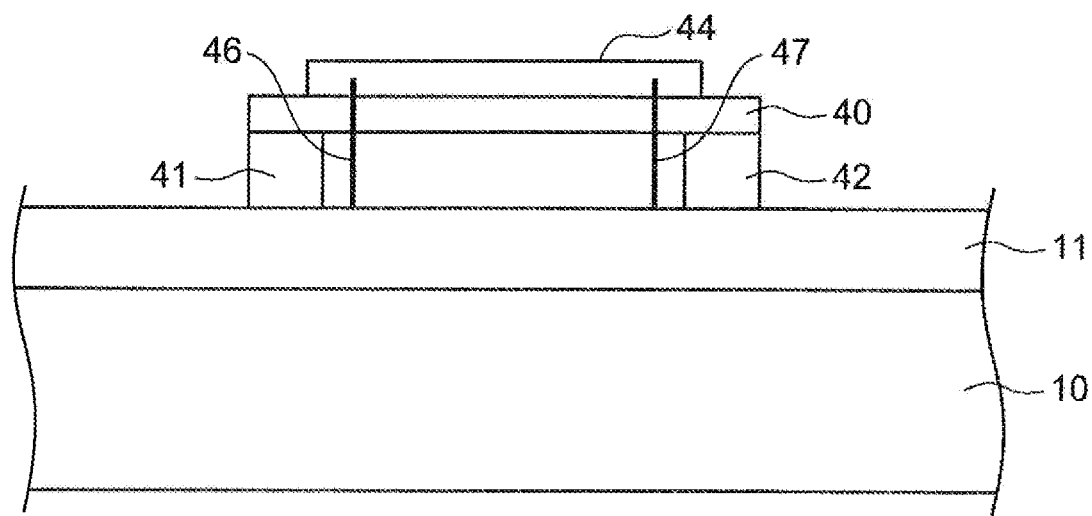

The structure of the humidity sensor 31 is now described with reference to FIGS. 5A and 5B. FIG. 5A illustrates, on an enlarged scale, a main part of the humidity sensor 31 disposed inside the windshield 10, as viewed from the vehicle cabin, along arrow A in FIG. 1. FIG. 5B illustrates the main part of the humidity sensor 31 viewed along arrow B in FIG. 5A.

The humidity sensor 31 is, for example, a polymer-based resistive humidity sensor. The humidity sensor 31 includes a base material 40, a humidity sensitive film 44 supported on the base material 40, and a pair of electrodes 46 and 47 connected together through the humidity sensitive film 44.

The base material 40 is attached to the surface of the antifogging coating 11 facing the vehicle cabin, via, for example, a pair of spacers 41 and 42. The spacers 41 and 42 are fixed to the antifogging coating 11 with an adhesive or the like. The spacers 41 and 42 are arranged in, for example, the vehicle body width direction, with an interval therebetween. The spacers 41 and 42 are, for example, bar-shaped members, and arranged parallel to each other. The spacers 41 and 42 interposed between the base member 40 and the antifogging coating 11 ensure a space through which the airflow supplied from the air conditioner 20 passes.

The electrodes 46 and 47, each having the shape of comb teeth, are arranged on a surface of the base member 40 opposite to the antifogging coating 11 such that they are out of contact with each other. The humidity sensitive film 44 is made of, for example, a macromolecular polymer. The humidity sensitive film 44 is formed on the surface of the base material 40 opposite to the antifogging coating 11.

When the quantity of water absorbed in the humidity sensitive film 44 increases, the electric resistance value between the electrodes 46 and 47 decreases due to increase in mobile ions in the humidity sensitive film 44. Thus, the humidity sensor 31 is capable of detecting a humidity in a part, of the vehicle cabin space, in which the humidity sensitive film 44 is located, based on the electric resistance value between the electrodes 46 and 47.

The humidity sensitive film 44 is disposed in the temperature boundary layer X. More specifically, the humidity sensitive film 44 is disposed at a position preferably within 3 mm, and more preferably within 1 mm from the surface of the antifogging coating 11 facing the vehicle cabin (see FIG. 4).

In one preferred embodiment, the humidity sensitive film 44 is disposed at a distance of 0.05 mm or more from the surface of the antifogging coating 11 facing the vehicle cabin, within the temperature boundary layer X. This configuration can effectively prevent the airflow along the antifogging coating 11 from being hindered by the base material 40 and the humidity sensitive film 44, and enables accurate detection of the humidity of the temperature boundary layer X.

When moisture in the air in the vehicle cabin space adheres to the surface of the antifogging coating 11, the moisture is absorbed into the antifogging coating 11. At this time, the temperature boundary layer X facing the antifogging coating 11 is in a state in which the humidity is less likely to increase because the moisture in the air is absorbed into the antifogging coating 11.

However, when the antifogging coating 11 absorbs water in a quantity equal to or higher than its absorption capacity and consequently becomes saturated, the humidity in the temperature boundary layer X becomes likely to increase. Thus, as the quantity of water absorbed in the antifogging coating 11 increases, it becomes more likely that the humidity in the temperature boundary layer X reaches or exceeds the threshold described above. When the humidity in the temperature boundary layer X becomes equal to or higher than the threshold, the control unit 32 operates the air conditioner 20 to supply conditioning airflow from the defroster air outlet 21 toward the antifogging coating 11. As a result, the water absorbed in the antifogging coating 11 is vaporized to substantially prevent fog on the surface of the antifogging coating 11, thereby ensuring the passenger's field of view.

In the first embodiment described above, the polymer-based resistive humidity sensor 31 is used as an example. However, the humidity sensor is not limited to any particular type. For example, a polymer-based capacitive humidity sensor 131 illustrated in FIGS. 6A and 6B may be used instead of the polymer-based resistive humidity sensor 31.

Figure 6A:
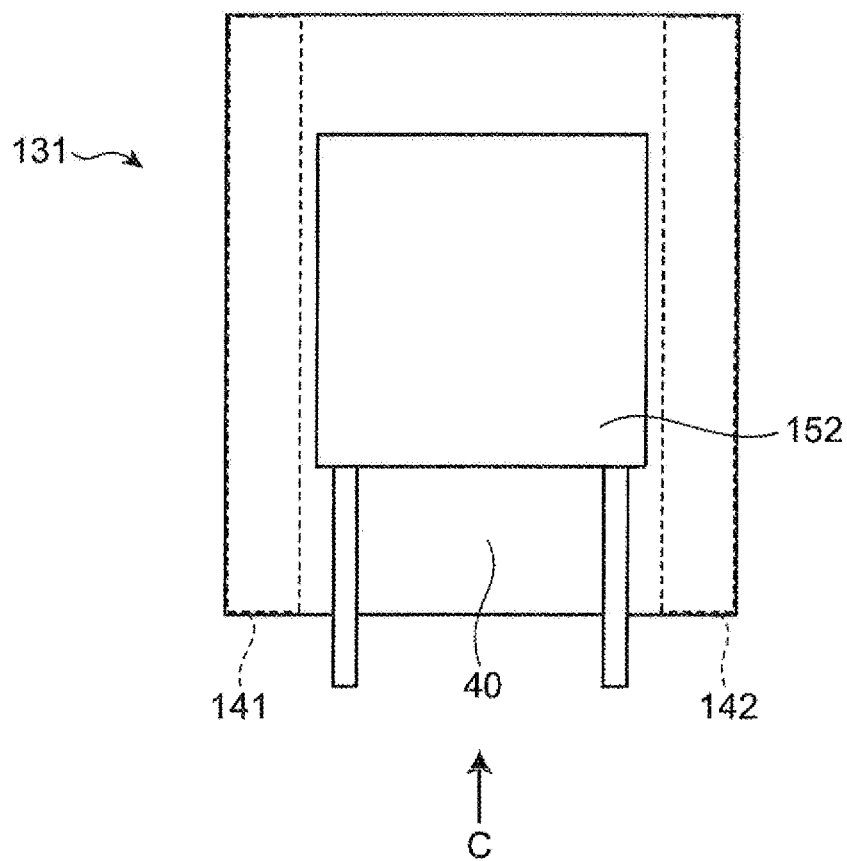
FIGS. 6A and 6B are diagrams illustrating an exemplary structure of a polymer-based capacitive humidity sensor.
Figure 6B:
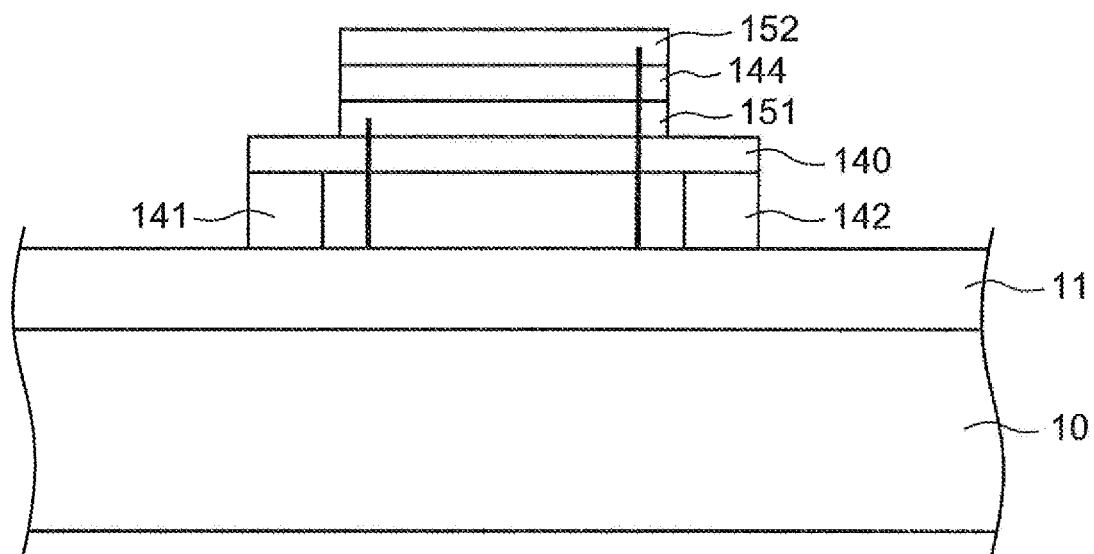

Just like the first embodiment, FIG. 6A illustrates, on an enlarged scale, a main part of the humidity sensor 131 disposed inside the windshield 10, as viewed from the vehicle cabin along arrow A in FIG. 1. FIG. 6B illustrates the main part of the humidity sensor 131 viewed along arrow C in FIG. 6A.

The polymer-based capacitive humidity sensor 131 illustrated in FIGS. 6A and 6B includes a base material 140, a humidity sensitive film 144 functioning as a dielectric and supported on the base material 140, and a first electrode 151 and a second electrode 152 facing each other with the humidity sensitive film 144 interposed therebetween.

The base material 140 is attached to the surface of the antifogging coating 11 facing the vehicle cabin, via, for example, a pair of spacers 141 and 142. The spacers 141 and 142 have, for example, a configuration similar to that of the spacers 41 and 42 of the polymer-based resistive humidity sensor 31 described above, so that a space through which the airflow supplied from the air conditioner 20 passes can be ensured between the base material 140 and the antifogging coating 11.

The first electrode 151, the humidity sensitive film 144, and the second electrode 152 are stacked on top the other in this order over a surface of the base material 140 opposite to the antifogging coating 11. The humidity sensitive film 144 is made of a polymer, such as cellulose or PVA.

When the quantity of water absorbed in the humidity sensitive film 144 increases or decreases, the electric resistance value between the first and the second electrodes 151 and 152 varies. Thus, the humidity sensor 131 is capable of detecting a humidity in a part, of the vehicle cabin space, in which the humidity sensitive film 144 is located, based on the electric resistance value between the first and the second electrodes 151 and 152.

Also with the polymer-based capacitive humidity sensor 131, which has the humidity sensitive film 144 disposed in the temperature boundary layer X, just like the humidity sensor described above, enables accurate detection of the humidity in the temperature boundary layer X.

Next, a vehicle antifogging system 230 according to a second embodiment will be described with reference to FIGS. 7 to 9. Components similar to those of the first embodiment are denoted by the same reference characters, and explanation thereof is not repeated.

Figure 7:
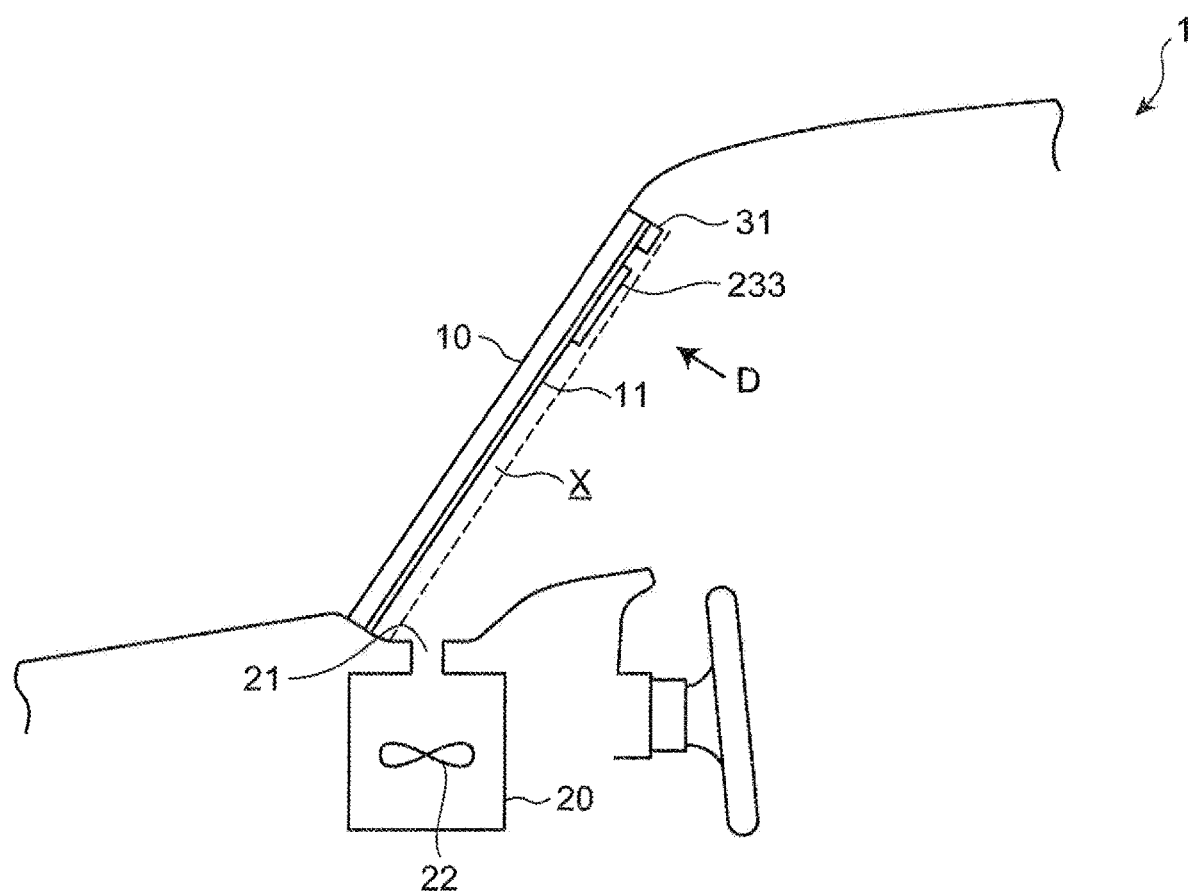
FIG. 7 is a schematic side view of a vehicle including an antifogging coating according to a second embodiment.
Figure 8:
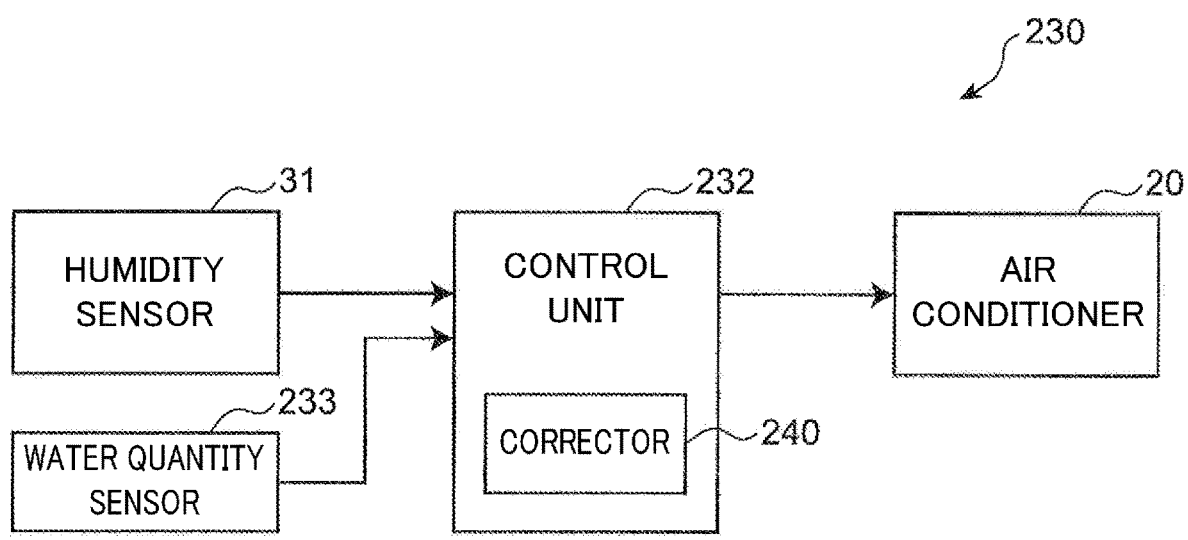
FIG. 8 is a system diagram of a vehicle antifogging system including the antifogging coating according to the second embodiment.

As illustrated in FIGS. 7 and 8, the antifogging system 230 includes, in addition to an antifogging coating 11, an air conditioner 20, a humidity sensor 31, and a control unit 232 that are similar to those of the first embodiment, a water quantity sensor 233 detecting the quantity of water in the antifogging coating 11. The water quantity detected by the water quantity sensor 233 is output to the control unit 232.

Figure 9A:
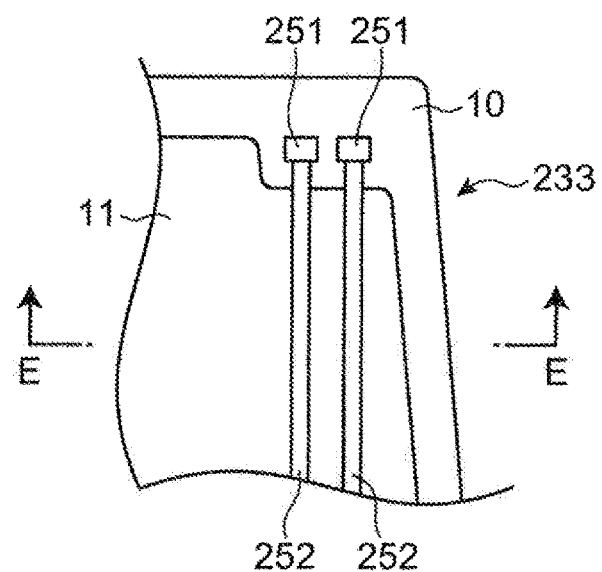
FIGS. 9A and 9B are diagrams showing, on an enlarged scale, a main part of a water quantity sensor according to the second embodiment.
Figure 9B:
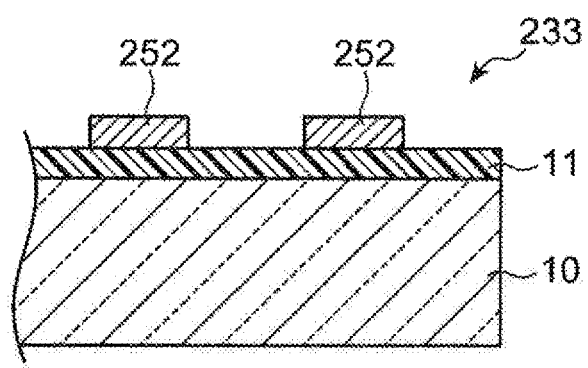

Here, an exemplary structure of the water quantity sensor 233 is described with reference to FIGS. 9A and 9B. FIG. 9A illustrates, on an enlarged scale, a main part of the water quantity sensor 233, as viewed along arrow D in FIG. 7, and FIG. 9B is a cross-sectional view taken along line E-E in FIG. 9A.

The water quantity sensor 233 includes a pair of electrodes 251 and 251 and a pair of conductors 252 and 252 extending in, for example, a straight line from the respective electrodes 251 and 251. The electrodes 251 and 251 are connected to the control unit 232 through respective lead wires (not illustrated).

The conductors 252 and 252 are attached, with an interval therebetween, to the antifogging coating 11. The conductors 252 and 252 are fixed to the surface of the antifogging coating 11 facing the vehicle cabin, with an adhesive or the like.

The antifogging coating 11 functions as a dielectric between the conductors 252 and 252 of the water quantity sensor 233, and the conductors 252 and 252 are capacitively coupled together to form a capacitor. The water quantity sensor 233 outputs a capacitance value between the conductors 252 and 252 to the control unit 232.

The control unit 232 includes a corrector 240 which corrects a humidity R detected by the humidity sensor 31. The corrector 240 corrects the humidity R based on the water quantity detected by the water quantity sensor 233 to calculate corrected humidity R'.

In this embodiment, the corrector 240 calculates the corrected humidity R', based on a percentage of water absorption α of the antifogging coating 11 calculated from the water quantity in the antifogging coating 11 detected by the water quantity sensor 233, the humidity R detected by the humidity sensor 31, a constant β corresponding to the water absorptivity of the antifogging coating 11, and according to following Expression 4.

$$R' = R - \beta(1-\alpha) \tag{4}$$

The percentage of water absorption α indicates a ratio of the current water quantity of the antifogging coating 11 detected by the water quantity sensor 233 to the saturated water absorption volume of the antifogging coating 11, whereas the value given by 1−α indicates a ratio of a remaining quantity to the saturated water absorption volume of the antifogging coating 11. A value obtained by multiplying the ratio of the remaining quantity by the constant β corresponding to the water absorptivity of the antifogging coating 11 is subtracted from the current humidity R, thereby correcting the humidity R to corrected humidity R'.

The corrected humidity R' calculated in this manner is a parameter indicating likelihood of occurrence of fog on the surface of the antifogging coating 11, with the humidity R in the temperature boundary layer X detected by the humidity sensor 31, and the current water absorptivity of the antifogging coating 11 taken into account.

In the second embodiment, the control unit 232 performs control to operate the air conditioner 20 when the corrected humidity R' is equal to or higher than a predetermined threshold. This configuration enables more minute control of the operation of the air conditioner 20.

In this embodiment, the air conditioner 20 is used as the dryer. Alternatively, a conductor may generate heat. The conductor may be provided inside the windshield 10 or at the interface between the windshield 10 and the antifogging coating 11. In this case, a conventional electric heater can be used as the conductor. By contrast, the conductor may be provided at the interface between the windshield 10 and the antifogging coating 11, or on the surface of the antifogging coating 11 facing the vehicle cabin. In this case, the antifogging coating can be directly heated, enabling effective removal of the water absorbed in the antifogging coating. Note that the interface between the windshield 10 and the antifogging coating 11 refers to a plane between the surface of the windshield 10 facing the vehicle cabin and the antifogging coating 11.

What is claimed is:

1. A vehicle antifogging system comprising:
   a window provided between a space inside a vehicle cabin and a space outside the vehicle cabin;
   an antifogging coating provided on a surface of the window facing the vehicle cabin, and configured to absorb water adhering to a surface of the antifogging coating into the antifogging coating;
   a dryer configured to vaporize the water absorbed in the antifogging coating;
   a humidity detector configured to detect a humidity in a temperature boundary layer formed along a surface of the antifogging coating facing the vehicle cabin;
   a controller configured to receive a signal from the humidity detector and output a signal to the dryer to operate the dryer; and
   a water quantity detector configured to detect a quantity of water absorbed in the antifogging coating, wherein
   the controller is configured to output a signal to the dryer to operate the dryer when the humidity is equal to or higher than a predetermined threshold, the controller is configured to receive a signal from the water quantity detector, and perform a calculation to correct the humidity on the basis of the water quantity, and the controller is configured to operate the dryer when the corrected humidity is equal to or higher than the threshold.

2. The vehicle antifogging system of claim 1, wherein the humidity detector is configured to detect the humidity in a part of the space inside the vehicle cabin, the part extending 3 mm or less from the surface of the antifogging coating facing the vehicle cabin.

3. The vehicle antifogging system of claim 2, wherein the humidity detector is positioned at a distance of 0.05 mm or more from the surface of the antifogging coating facing the vehicle cabin.

4. The vehicle antifogging system of claim 1, wherein the dryer is configured to blow dry air over the surface of the antifogging coating.

5. The vehicle antifogging system of claim 1, wherein the dryer is provided on the window, and is configured to generate heat by causing a current to flow through a conductor, and the conductor is provided inside the window, at an interface between the window and the antifogging coating, or on the surface of the antifogging coating facing the vehicle cabin.

6. The vehicle antifogging system of claim 1, wherein the window is made of light-transmitting glass or resin.

\* \* \* \* \*